United States Patent [19]

Samochocka

[11] 4,313,926

[45] Feb. 2, 1982

[54] METHOD FOR THE PREPARATION OF A SCINTILLOGRAPHIC AGENT

[75] Inventor: Krystyna Samochocka, Warsaw, Poland

[73] Assignee: Uniwersytet Warszawski, Warsaw, Poland

[21] Appl. No.: 28,299

[22] Filed: Apr. 9, 1979

[30] Foreign Application Priority Data

Apr. 10, 1978 [PL] Poland ................................ 205961

[51] Int. Cl.$^3$ .................... A61K 49/00; A61K 43/00; C07F 13/00
[52] U.S. Cl. ...................................... 424/1; 260/429 J; 562/433; 562/571; 424/9
[58] Field of Search ...................... 562/433, 480, 571; 424/1, 1.5, 9; 260/429 J

[56] References Cited

U.S. PATENT DOCUMENTS

| | | | |
|---|---|---|---|
| 2,239,617 | 4/1941 | Moore | 562/571 |
| 2,781,391 | 2/1957 | Mannheimer | 562/433 X |
| 2,895,989 | 7/1959 | Sexton | 562/571 |
| 4,017,956 | 4/1977 | Loberg et al. | 424/1 |

OTHER PUBLICATIONS

"Solco Hida $^{99m}$Tc.", Catalogue of Sollo of Basel, Switzerland.

*Primary Examiner*—Edward A. Miller
*Assistant Examiner*—Christine M. Nucker
*Attorney, Agent, or Firm*—Ladas & Parry

[57] ABSTRACT

The invention relates to a method for the preparation of a scintillographic agent which comprises preparing a derivative of iminodiacetic acid particularly an $\omega$-chlor-2,4-dimethylacetanilide derivative, and chelating such derivative with a radiometal. The scintillographic agent is adapted for intravenous administration in medical diagnostics, in particular for the diagnosis of the bile canal.

4 Claims, No Drawings

METHOD FOR THE PREPARATION OF A SCINTILLOGRAPHIC AGENT

FIELD OF TECHNIQUE

This invention relates to a method for the preparation of a scintillographic agent which comprises a chelate of an iminodiacetic acid derivative with a radiometal. More particularly, the invention is concerned with the preparation of a scintillographic agent comprising a 2,4-dimethylaniline derivative chelated with a radiometal, particularly technitium 99 m Tc radiometals. The product of the invention is adapted for intravenous administration in medical diagnostics, in particular for the diagnostics of the bile canal.

TECHNICAL BACKGROUND

The known method for the preparation of a scintillographic agent, which is a derivative of iminodiacetic acid chelated with technetium 99 m Tc, comprises treating 2,6-diethylaniline or 2,6-dimethylaniline dissolved in acetic acid with chloracetyl chloride at a temperature of 10° C. and then with a solution of sodium acetate. The mixture is shaken for 30 minutes. The resulting sediment is dissolved in a benzene diethylamine solution and this solution is warmed during several hours under a water circulation cooler. Hereafter the diethylamine hydrochloride is separated and the solution is extracted with hydrochloric acid. Then alkali is added to the extract which is extracted with ether. The obtained ether solution is distilled and the product of distillation is ω-chlor-2,6-diethylacetanilide. The yield in this process is about 70 %. Further, the ω-chlor-2,6-diethylacetanilide together with the sodium salt of iminodiacetic acid is dissolved in 75 % alcohol. The mixture is warmed during about two days under a water circulation cooler and, after evaporating the solvent, the dry sediment is dissolved in water and twice extracted with ether. After removing the ether extract, hydrochloric acid is added until pH reaches about 3.2 and the precipitated sediment is crystallized from water. The derivative of the iminodiacetic acid, produced in this way, is once more dissolved in water and, after the addition of stannous chloride in 1 n hydrochloric acid the pH value is adjusted to about 5,5 by the addition of sodium hydroxide. The solution is then clarified through a sterile filter, freeze-dried and stored in sterile ampoules fixed in nitrogen or filled at a reduced pressure. Just before an intravenous administration a sterile pertechnetate 99 m Tc solution is added to the derivative of the iminodiacetic acid. The durability of the scintillographic agent produced in that way is 6 hours.

THE SUBSTANCE OF THE INVENTION

Surprisingly it has been found, through examination and tests, that a better radiochemical durability and better biological and scintillographical results are achieved by the use of a derivative of iminodiacetic acid containing methyl groups are at the second and the fourth carbon atom of the aromatic ring, and by an improved method for the preparation of this agent.

In accordance with the present invention there is provided a method for the preparation of a scintillographic agent which comprises dissolving 2,4-dimethylaniline in acetic acid at room temperature, mixing the resulting solution with chloracetyl chloride under vigorous mixing. The solution then is kept several hours at a temperature of 4° C. The reaction mixture is poured into water with ice. The sediment is crystallized from alcohol and from post-crystallizatic bases, diluted in water, a further quantity of sediment is regained which gives a total yield 80 to 82 %. The ω-chloracetanilide produced in this way is dissolved, together with the sodium salt of iminodiacetic acid, in aqueous ethanol wherein the proportion by volume of water to ethanol is 1:1.2. The mixture is warmed during several hours under a water circulation cooler. After the evaporation of solvent, the dry sediment is dissolved in water, the non-reacted component is separated, and the residual water solution is adjusted to the pH value about 2.5. The precipitated sediment is dissolved in absolute ethanol, non-reacted component is separated and, after the evaporation of solvent, the derivative of iminodiacetic acid is crystallized from water at pH about 2.5. The yield is 25 to 35 %. Further, the derivative of iminodiacetic acid, produced in this way, is dissolved in water with a possible addition of stannous chloride in hydrochloric acid and the pH value is adjusted to 4 to 6 depending on the supplied chelating radiometal. The solution is then passed through a sterile filter, freeze-dried and stored in sterile ampoules fixed in nitrogen or filled at a reduced pressure. At least half an hour prior to an intravenous administration the sterile solution of pertechnetate 99 m Tc or another radiometal is added to the derivative of iminodiacetic acid. The scintillographic agent according to the invention is durable up to 24 hours.

EXAMPLE

To 0.12 mole of 2,4-dimethylaniline dissolved in acetic acid 0.13 mole of chloracetyl chloride was added at a room temperature under vigorous mixing both components during 5 to 10 minutes. The reacting mixture was kept 3 to 4 hours at a temperature of 4° C. and then poured into water with ice. Sediment was extracted of water and crystallized from ethanol. A further quantity of sediment was regained from post-crystallization bases after dissolving them in water which made a total yield 19.5 g or 82 %. The ω-chlor-2,4-dimethylacetanilide in a quantity of 40 moles obtained in this way was dissolved together with 40 moles of the sodium salt of iminodiacetic acid in 250 ml of diluted ethanol. The proportion by volume of water to ethanol was 1:1.2. The mixture was warmed on a water bath during 6 hours under a water circulation cooler. After the evaporation of solvent, the dry residue was dissolved in water, the non-reacted component was separated and the water solution was adjusted with hydrochloric acid to the pH value about 2.5. The deposited sediment was dissolved in absolute ethanol and, after the separation of solvent, the derivative of iminodiacetic acid was crystallized from water. The yield was about 30 %. Further, 1 mg of N-/2,4-dimethylphenyl-carbamoylmethyl/-iminodiacetic acid, obtained in this way, was dissolved in 1 ml 0.1 N NaOH, the pH value of the solution was adjusted to 5.5 and then 0.02 mg of stannous chloride in 1 n hydrochloric acid was added and the pH value of the solution was adjusted to about 4 dosing a solution of 0.1 n sodium hydroxide. After a thorough mixing and 15 minutes incubation 0.5 ml of pertechnetate of 1 mCi radioactivity was added. The durability of the chelate was measured with the method of high tension paper electrophoresis in connection with the radiochromatographic detection with the Packard apparatus. For biological and scintillographical examinations 10 mg samples of the N-2,4-dimethylphenyl-carbamoylmethyl/-iminodiacetic acid were prepared, to each of them 0.2 mg stannous chloride in 1 n hydrochloric acid was added, passed through a sterile filter and then freeze-dried and stored at 4° C. in sterile ampoules fixed in nitrogen.

We claim:

1. A method for the preparation of a scintillographic agent which comprises dissolving 2,4-dimethylaniline in acetic acid at room temperature, mixing the resulting solution with chloracetyl chloride, crystallizing the sediment from ethanol and regaining a further quantity of acetanilide from postcrystallization bases, dissolving the resulting ω-chlor-2,4-dimethylactanilide derivative together with the sodium salt of iminodiacetic acid in aqueous ethanol, the proportion by volume of water to ethanol being 1:1.2, heating the solution for several hours, evaporating the solvent, dissolving the dry residue, separating the non-reacted component and adjusting the pH of the remaining solution to a value of about 2.5 with hydrochloric acid, dissolving the precipitated sediment, evaporating the solvent and crystallizing the said derivative from water or from a 25% aqueous solution of sodium acetate, dissolving the derivative once more in an aqueous solution of sodium hydroxide or in water, again adjusting the pH to a value of 4 to 6, passing the solution through a sterile filter, freeze-drying and keeping it in sterile ampoules, and finally, prior to administration, chelating the obtained derivative of iminodiacetic acid with a radiometal.

2. A method according to claim 1, in which stannous chloride in hydrochloric acid is added to the solution prior to the second pH adjustment.

3. A process according to claim 1, in which the 2,4-dimethylaniline is dissolved in acetic acid and mixed with chloracetyl chloride at room temperature, the aqueous ethanol solution, in which the chloracetanilide derivative is dissolved together with the sodium salt of iminodiacetic acid, has a volume ratio 1 part of water to 1.2 parts of ethanol, the mixture is heated on a water bath for 6 hours under a water cooler, the non-reacting agent is separated and the pH value of the solution is immediately adjusted to 2.5, the precipitated sediment is dissolved in absolute ethanol, and the resulting derivative of iminodiacetic acid is chelated with a radiometal from half an hour to 24 hours prior to an intravenous administration of the agent into the organism.

4. A method according to claim 1, in which the radiometal is technetian 99 m Tc.

* * * * *